United States Patent [19]

Yamada et al.

[11] Patent Number: 5,120,651
[45] Date of Patent: Jun. 9, 1992

[54] RESTRICTION ENZYME AGEI AND PROCESS FOR PRODUCING SAME

[75] Inventors: Yuzo Yamada, Fujieda; Hirofumi Mizuno, Shizuoka; Kazuhide Yamasato, Matsudo, all of Japan

[73] Assignee: Nisshin Seito Kabushiki Kaisha, Tokyo, Japan

[21] Appl. No.: 499,655

[22] Filed: Mar. 27, 1990

[30] Foreign Application Priority Data

Mar. 29, 1989 [JP] Japan .................................. 1-77817

[51] Int. Cl.$^5$ .............................................. C12N 9/22
[52] U.S. Cl. ........................................ 435/199; 435/91
[58] Field of Search ................................... 435/199, 91

[56] References Cited

U.S. PATENT DOCUMENTS

| 4,588,689 | 3/1984 | Kado et al. | 435/199 |
| 4,668,631 | 9/1985 | Obayashi et al. | 435/199 |
| 4,746,609 | 6/1985 | Bolton et al. | 435/91 |
| 4,840,901 | 5/1988 | Grosskopf et al. | 435/91 |
| 4,871,664 | 2/1987 | Brown et al. | 435/91 |

OTHER PUBLICATIONS

Yamada, Y. et al (1989) Agric. Biol. Chem. 53(6), 1747-1749.
Appendix, p. 98, New England BioLabs® Catalog (1988-1989).

Primary Examiner—Charles L. Patterson, Jr.
Attorney, Agent, or Firm—Christensen, O'Connor, Johnson & Kindness

[57] ABSTRACT

A restriction enzyme capable of recognizing and cleaving a DNA sequence at a position indicated by the arrows:

5'-A↓CCGGT-3'

3'-TGGCC↑A-5'.

3 Claims, No Drawings

RESTRICTION ENZYME AGEI AND PROCESS FOR PRODUCING SAME

FIELD OF THE INVENTION

This invention relates to a new restriction enzyme and a process for producing same.

BACKGROUND OF THE INVENTION

Restriction enzymes are endonucleases that are capable of recognizing a specific sequence of bases on a deoxyribonucleic acid (DNA) molecule and of cleaving the double-stranded DNA chain within or near the specific site. These enzymes have high substrate specificities and reproducibilities, so that they are indispensable in gene manipulation such as mass production of genetic materials, gene isolation, analyses of base sequences, and structural protein analyses. Furthermore, they are reagents having important application in the assessment and treatment of genetic diseases, and artificial gene transformation.

About 100 kinds of restriction enzymes have so far been isolated from various microorganisms, each being identified by the specific base sequence it recognizes and by the cleavage pattern it exhibits.

However, the number of restriction enzyme species yet discovered is only about half the theoretical estimate.

Accordingly, this invention is to provide a novel restriction enzyme having a novel recognition base sequence and an industrial process for producing same.

DESCRIPTION OF THE INVENTION

The present inventors have been investigating numerous microorganisms capable of producing restriction enzymes, for the purpose of developing useful restriction enzymes. During the course of these studies, the inventors have discovered that a microorganism belonging to the genus Agrobacterium produces a novel restriction enzyme capable of recognizing a new base sequence which has previously been totally unknown.

A novel restriction enzyme AgeI according to the present invention has the following properties:

(a) Action and Substrate Specificity:

Recognizes the base sequence in a double-stranded deoxyribonucleic acid molecule as shown below, and cleaves it at the arrow-marked sites:

5'-A ↓ CCGGT-3'

3'-TGGCC ↑ A-5'

(wherein A, G, T and C represent adenosine, guanosine, thymidine and cytidine, respectively). In order to determine the recognition base sequence of the restriction enzyme AgeI, the number of cleavage sites of *Escherichia coli* (*E. coli*) phage λDNA, *E. coli* phage φX174 RF DNA, *E. coli* phage M13 mp18 RF DNA, and *E. coli* plasmid pBR322 DNA was studied. As a result, only λDNA was cleaved at 1-15 sites but no other DNAs were cleaved. Comparing this with data by Fuchs (*Gene*, 10:371, 1980), the restriction enzyme AgeI was inferred to cleave either the base sequence 5'-ACCGGT-3' or the sequence 5'-ATGCAT-3'.

After double digestion of DNA with a restriction enzyme AgeI and a restriction enzyme EcoT22I which recognizes and cleaves a base sequence 5'-ATGCAT-3', there were obtained cleavage fragments different from those generated by the restriction enzyme AgeI digestion alone and thus, it was clear that the restriction enzyme AgeI did not recognize the base sequence 5'-ATGCAT-3'.

The cleavage sites were determined by the following method. *E. coli* plasmid pBR328 DNA having a single cleavage site produced by the restriction enzyme AgeI, was cleaved by the restriction enzyme AgeI and phosphate at the cleaved terminal end was removed with alkaline phosphatase. The DNA fragment thus obtained was labeled with radioactive phosphate at the 5'-terminal end, using polynucleotide kinase and [γ-$^{32}$P] adenosine triphosphate. The DNA fragment labeled with radioactive phosphate was digested with the restriction enzyme EcoRI, giving two fragments, which were separated and obtained using polyacrylamide gel electrophoresis. Each DNA fragment was sequenced by the method of Maxam and Gilbert, starting at its 5'-terminal end. These experiments indicated that the restriction enzyme AgeI recognizes the following base sequence:

5'-A ↓ CCGGT-3'

3'-TGGCC ↑ A-5' and cleaves it at the arrow-marked sites.

(b) Optimal Conditions for Enzymatic Activity and Enzyme Stability:

Optimal pH: The restriction enzyme AgeI had an optimal pH of 7.5.

Stable pH range: The restriction enzyme AgeI was stable over the pH range of 5.0–8.0 at 4° C. for 24 hours.

Optimal temperature: The restriction enzyme AgeI had the optimal temperature of 30° C.

Thermal stability: It exhibited high activities upon heating even at 45° C. for 5 minutes.

Stable salt concentration: It exhibited high activities in 0–150 mM NaCl.

Molecular weight: Molecular weight of the enzyme was calculated to be 23,000 and 24,000 by the gel filtration method using Superose 12 HR 10/30 (manufactured by Pharmacia LKB Biotechnology) and the SDS-PAGE (sodium dodecyl sulfate-polyacrylamide gel disk electrophoresis) method, using 0.1% SDS and 12.5% T running gel, respectively.

A process of the present invention for producing the restriction enzyme AgeI, comprises growing a microorganism, belonging to the genus Agrobacterium, which is capable of producing AgeI, in a culture medium, and collecting the enzyme thus formed from the culture broth.

Any microorganism belonging to the genus Agrobacterium, capable of producing AgeI, may be used; a typical example is *Agrobacterium gelatinovorum* IAM 12617 separated from saltwater (sea water), which is stored in the Institutes of Applied Microbiology, the University of Tokyo. Other Agrobacterium strains that produce AgeI may readily be determined by carrying out steps analogous to those in the Examples section herein and testing for AgeI, e.g., by assaying for its enzymatic activity using an appropriate substrate containing the recognition sequence identified herein. The culture method is not limited and any culture method currently used for growing microorganisms belonging to the genus Agrobacterium may be used.

Peptone, amino acid and yeast extract as carbon and nitrogen sources, sugars such as glucose and organic acids as other carbon sources, inorganic salts such as ammonium sulfate and sodium nitrate as other nitrogen sources and sodium chloride, magnesium chloride and potassium phosphate as other inorganic salts, may be utilized.

AgeI can be extracted and purified by known techniques commonly used for restriction enzymes. The cultured microorganisms are harvested by routine methods and then disrupted by sonication, etc., followed by centrifugation to give a cell-free extract. The extract is purified by combined column chromatographies such as ion exchange column chromatography, hydroxyapatite column chromatography, gel filtration, affinity column chromatography, and the like, to afford the restriction enzyme AgeI.

The activity of AgeI was determined according to the method described hereinafter. The enzyme was added to a reaction mixture containing 10 mM Tris-HCl (pH 7.5), 7 mM 2-mercaptoethanol, 7 mM magnesium chloride, 50 mM sodium chloride and 1 µg λDNA, to a final volume of 50 µl, and incubated at 37° C. for 1 hour. The reaction was stopped by the addition of 5 µl of the stop solution containing 1% SDS (sodium dodecyl sulfate), 50% glycerol and 0.1% BPB (bromophenol blue). E. coli phage λDNA in the reaction solution was separated with 1% agarose gel electrophoresis containing 0.5 µg/ml ethidium bromide. Electrophoresis was regarded as complete when the number and intensity of the bands obtained by UV radiation produced by DNA fragments was constant.

The enzyme activity which ensures complete digestion of 1 µg λDNA in the above reaction was defined as one unit.

EXAMPLE

*Agrobacterium gelatinovorum* IAM 12617 was cultured in a modified saltwater slant medium containing 1.5% agarose (Table 1) at 30° C. for 48 hours and stored at 4° C. A portion of the stored microorganisms was inoculated in the modified saltwater medium and precultured under shaking at 30° C. for 24–48 hours. The precultured medium was added to the present culture medium in a ratio of 1:10 for culture under shaking at 30° C. for 24 hours. The wet microbial cells of about 25 g were harvested by centrifugation.

TABLE 1

| Compositions per 1 l of the modified saltwater medium (pH 7.5) | |
|---|---|
| Peptone | 5.0 g |
| Yeast extract | 1.0 g |
| Saltwater | 750 ml |

To the obtained microbial cells was added 200 ml of buffer solution A (10 mM Tris-HCl, pH 7.5, 7 mM 2-mercaptoethanol) and the cells were disrupted by sonication.

By centrifugation, a cell-free extract was obtained and sodium chloride was added thereto to have a final concentration of 100 mM. Then nucleic acids were removed with 1% streptomycin. Ammonium sulfate was added to the resulting solution to 25–55% (w/v), and the precipitate was obtained as the restriction enzyme fraction. The restriction enzyme fraction was dissolved in 30 ml of buffer solution B (10 mM Tris-HCl, pH 7.5, 7 mM magnesium chloride, 7 mM 2-mercaptoethanol, 3% (v/v) glycerol) and then, dialyzed against 3 l of the same buffer solution.

The fraction obtained after dialysis was purified by each of the following column chromatographies (manufactured by Pharmacia Co.).

The dialysate was adsorbed on Heparin-Sepharose CL-6B (affinity chromatography) column chromatography equilibrated with buffer solution B. The adsorbed portion was eluted with buffer solution B. The adsorbed portion was eluted with buffer solution B containing sodium chloride using a linear gradient concentration of 0 to 1M. The restriction enzyme was obtained in fractions corresponding to 450 mM to 500 mM NaCl concentration. The restriction enzyme fraction was dialyzed against buffer solution B overnight.

The restriction enzyme fraction was adsorbed on DEAE-Sepharose CL-6B (ion exchange chromatography) column chromatography equilibrated with buffer solution B. The adsorbed portion was eluted with buffer solution B containing sodium chloride using a linear gradient concentration of 0 to 1M. The restriction enzyme was obtained in fractions corresponding to 200 mM to 250 mM NaCl concentration. The restriction enzyme fraction was dialyzed against 2 l of buffer solution B overnight.

The restriction enzyme fraction was adsorbed on Mono Q FPLC (ion exchange, Fast Protein Liquid Chromatography) equilibrated with buffer solution B. The adsorbed portion was eluted with buffer solution B containing sodium chloride using a linear gradient concentration of 0 to 600 mM. The restriction enzyme was obtained in fractions corresponding to 150 mM to 200 mM NaCl concentration.

The restriction enzyme fraction was dialyzed against buffer solution B containing 50% (v/v) glycerol overnight, affording the final standard sample of the enzyme. The final standard sample of the enzyme was free from extraneous nucleases and phosphatases.

The present invention has been described in relation to the various embodiments, including the preferred applications and parameters. One of ordinary skill in the art, after reading the foregoing specification, will be able to effect various changes, substitutions of equivalents, and other alterations without departing from the broad concept disclosed herein. For example, although the present invention has been described with reference to AgeI, it will be understood that other enzymes capable of recognizing and cleaving DNA at the recognition sequence disclosed herein form part of the present invention. In particular, structural variants of AgeI that share its specificity and activity are within the scope of this invention. It will also be understood that the enzymatic activity of these variants may be greater or less than, or equal to, that of AgeI with a given substrate.

The embodiments of the invention in which an exclusive property or privilege is claimed are defined as follows:

1. A restriction enzyme capable of recognizing and cleaving a DNA sequence at a position indicated by the arrows:

5'-A ↓ CCGGT-3'

3'-TGGCC ↑ A-5'.

2. A restriction enzyme, according to claim 1, having the following properties:
 (a) action and substrate specificity:

recognizes the base sequence in a double-stranded deoxyribonucleic acid molecule as shown below, and cleaves it at the arrow-marked sites:

5'-A ↓ CCGGT-3'

3'-TGGCC ↑ A-5' wherein A, G, T, and C represent adenosine, guanosine, thymidine, and cytidine, respectively;
(b) optimal pH:—7.5
(c) stable pH range:—5.0 to 8.0
(d) optimal temperature:—30° C.
(e) stable temperature:—45° C. by heating for at least 5 minutes
(f) stable salt concentration:—0–150 mM NaCl
(g) molecular weight:—23,000 as determined by gel filtration; 24,000 as determined by SDS-PAGE.

3. A process for producing the restriction enzyme AgeI, comprising growing a microorganism belonging to the genus Agrobacterium that is capable of producing AgeI in a culture medium, and collecting the enzyme thus formed from the culture broth.

* * * * *

UNITED STATES PATENT AND TRADEMARK OFFICE
CERTIFICATE OF CORRECTION

PATENT NO. : 5,120,651

DATED : June 9, 1992

INVENTOR(S) : Y. Yamada et al.

It is certified that error appears in the above-identified patent and that said Letters Patent is hereby corrected as shown below:

| COLUMN | LINE | |
|---|---|---|
| [57] Abstract | 6 | "t'-A↓CCGGT-3'" should be --5'-A↓CCGGT-3'-- |
| Claim 3 | 2 | "AgeI" should be --*AgeI*-- |
| Claim 3 | 3 | "Agrobacterium" should be --*Agrobacterium*-- |
| Claim 3 | 4 | "AgeI" should be --*AgeI*-- |

Signed and Sealed this

Twentieth Day of July, 1993

Attest:

MICHAEL K. KIRK

*Attesting Officer*   Acting Commissioner of Patents and Trademarks